US012083133B2

(12) United States Patent
Trasciatti

(10) Patent No.: US 12,083,133 B2
(45) Date of Patent: Sep. 10, 2024

(54) USE OF CHOLECALCIFEROL AS ADJUVANT IN THE TREATMENT OF MUSCULAR DYSTROPHIES

(71) Applicant: ABIOGEN PHARMA SPA, Pisa (IT)

(72) Inventor: Silvia Trasciatti, Vecchiano (IT)

(73) Assignee: ABIOGEN PHARMA SPA, Pisa (IT)

( * ) Notice: Subject to any disclaimer, the term of this patent is extended or adjusted under 35 U.S.C. 154(b) by 0 days.

(21) Appl. No.: 18/552,908

(22) PCT Filed: Mar. 25, 2022

(86) PCT No.: PCT/IB2022/052742
§ 371 (c)(1),
(2) Date: Sep. 28, 2023

(87) PCT Pub. No.: WO2022/208256
PCT Pub. Date: Oct. 6, 2022

(65) Prior Publication Data
US 2024/0100070 A1 Mar. 28, 2024

(30) Foreign Application Priority Data
Mar. 29, 2021 (IT) .......................... 102021000007655

(51) Int. Cl.
*A61K 31/593* (2006.01)
*A61P 21/00* (2006.01)
(52) U.S. Cl.
CPC ............ *A61K 31/593* (2013.01); *A61P 21/00* (2018.01)
(58) Field of Classification Search
CPC .............................. A61K 31/593; A61P 21/00
See application file for complete search history.

(56) References Cited

U.S. PATENT DOCUMENTS 10,045,999 B2   8/2018   Jourdan et al.
2011/0039810 A1   2/2011   Buck et al.

FOREIGN PATENT DOCUMENTS

CH        654206 A5 *   2/1986
WO   WO-2009101137 A1 *   8/2009   ........... A23L 33/155
WO   WO-2021086172 A1 *   5/2021   ............. A61K 31/19

OTHER PUBLICATIONS

Sgarbi, CH 654206 A5, English translation, publ. Feb. 14, 1986 (Year: 1986).*
Wicklund, Continuum (Minneap. Minn.), vol. 9(6), pp. 1535-1570, publ. 2013 (Year: 2013).*
Nair et al., J. of Basic & Clinical Pharmacy, vol. 7, pp. 27-31, publ. 2016 (Year: 2016).*
Alasady S H., "Effect of vitamin D on Becker muscular dystrophy: A review", Tropical Journal of Pharmaceutical Research, vol. 19, No. 12, Mar. 17, 2021, pp. 2691-2696.
De Luna N. et al., "1[alfpha], 25 (OH) 2-Vitamin D3 Increases Dysferlin Expression in Vitro and in a Human Clinical Trial", Molecular Therapy, vol. 20, No. 10, Oct. 1, 2012, pp. 1988-1997.
Search Report and Written Opinion of PCT/IB2022/052742 mailed Jul. 8, 2022.
Terracciano C et al., "Vitamin D deficiency in myotonic dystrophy type 1", Journal of Neurology, vol. 260, No. 9, Sep. 1, 2013, pp. 2330-2334.

* cited by examiner

*Primary Examiner* — Sarah Pihonak
(74) *Attorney, Agent, or Firm* — SILVIA SALVADORI, P.C.; Silvia Salvadori

(57) ABSTRACT

The use of cholecalciferol is described as an active agent or adjuvant in muscle regeneration and in the protection of muscle tissue in subjects suffering from muscular dystrophies. Also described are pharmaceutical compositions or food supplements including cholecalciferol and suitable excipients for use in the regeneration and protection of muscle tissue in subjects suffering from muscular dystrophies.

9 Claims, 6 Drawing Sheets

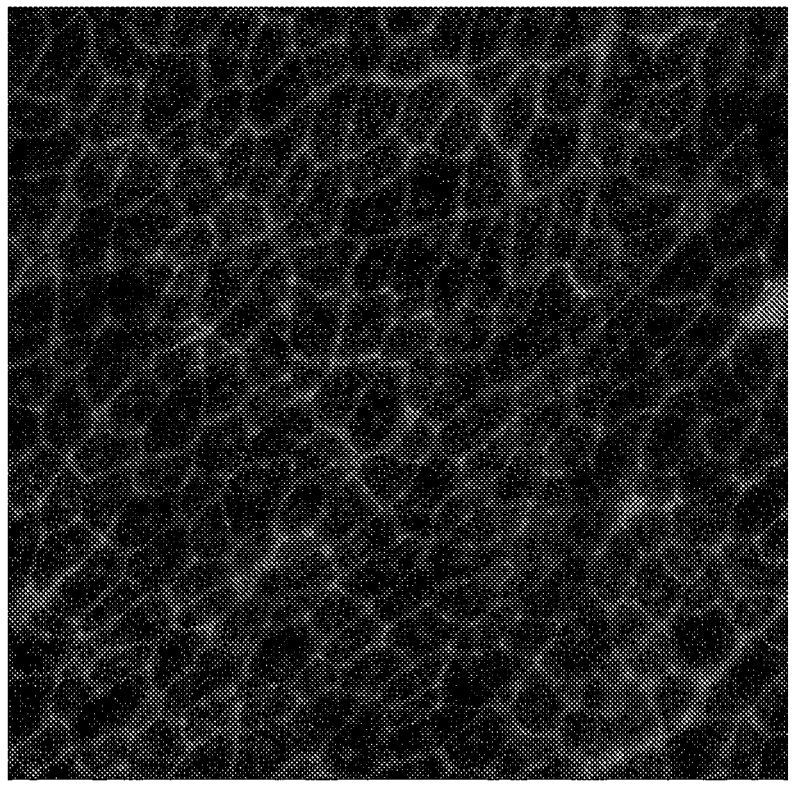
Fig. 7
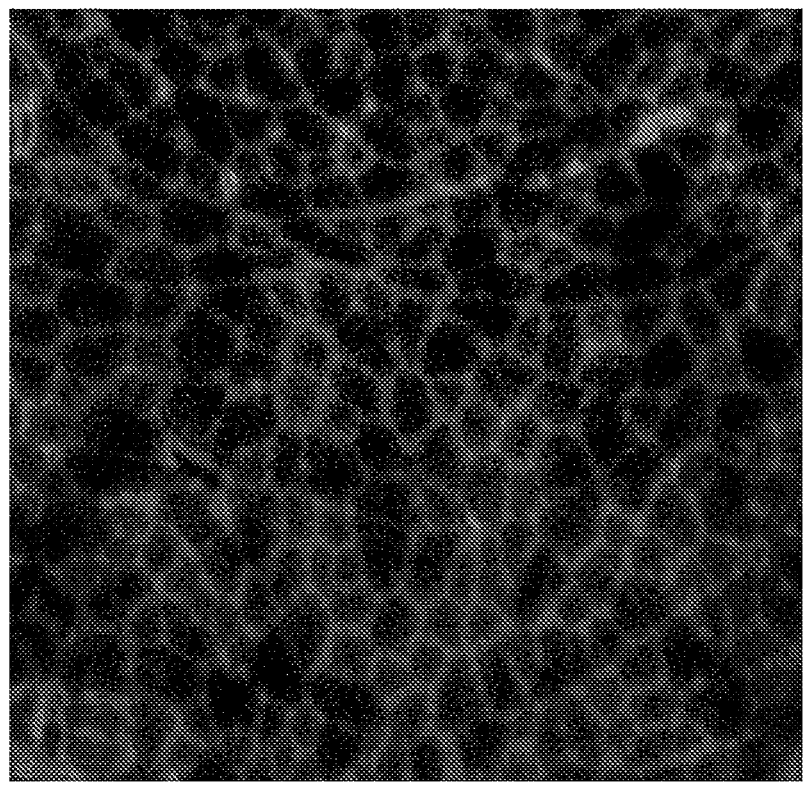
Figura 8

USE OF CHOLECALCIFEROL AS ADJUVANT IN THE TREATMENT OF MUSCULAR DYSTROPHIES

This application is a U.S. national stage of PCT/IB2022/052742 filed 25 Mar. 2022, which claims priority to and the benefit of Italian Application No. 102021000007655 filed 29 Mar. 2021, the contents of which are incorporated herein by reference in their entireties.

FIELD OF THE INVENTION

The present invention relates to the use of cholecalciferol as an active agent or adjuvant in the regeneration of muscle tissue in subjects suffering from muscular dystrophies.

STATE OF THE ART

Muscular dystrophies or prodegenerative diseases of the skeletal muscles are primary muscle disorders. The innervation of the affected muscles is in fact intact, while the muscle fibres are altered. Typical features of this group of diseases are the symmetrical distribution of muscle weakness and atrophy, while sensitivity is preserved and skin reflexes persist normally.

Muscular Dystrophies (DM) are inherited diseases caused by defects in several genes that result in loss of function, reduction or absence of proteins necessary for the proper functioning of muscle fibres. The consequence is a progressive degeneration of muscle tissue and a variable deficit of strength, entity, distribution and time of appearance.

In the recent history of dystrophies, the most notable event was the discovery by Kunkel in 1986 of the gene for dystrophin and its protein product. Since then, there has been an extraordinary accumulation of information on muscular dystrophies, from a genetic-molecular, ultrastructural and biochemical point of view, which has greatly expanded our knowledge of the mechanisms and causes of these diseases.

There are many forms of Dystrophy which are classified according to clinical criteria and the genetic defect.

Different types of muscular degenerative diseases have been identified and classified, from that of Emery-Dreyfuss, to Becker's dystrophy, to that of Duchenne. All three diseases have an early onset in affected subjects, usually before reaching adulthood.

There is no specific therapy for each of the muscular dystrophies. Various vitamins (including vitamin E), amino acids, testosterone, and drugs such as penicillamine, recommended in the past, have all proven ineffective.

Administration of prednisone appears to delay the progression time of Duchenne dystrophy for more than 3 years. The optimal dose is 0.75 mg/kg per day, but very often it is reduced due to the side effects of steroids, such as weight gain, Cushing's syndrome, behavioural and gastrointestinal disturbances.

New anti-inflammatory drugs, nitric oxide (NO) inhibitors, which seem to decrease muscle damage, are in the experimental phase, both clinical and preclinical.

Gene and stem cell therapies are also in an experimental phase.

The need is therefore strongly felt to develop drugs that are able to treat the aforementioned pathologies, or at least to counteract the harmful effects they cause, in particular the degeneration of muscle tissue.

The object of the present invention is therefore to find an effective remedy to promote the regeneration of muscle tissue in subjects suffering from muscular dystrophies, which is also well tolerated by the body.

SUMMARY OF THE INVENTION

This object was achieved through the use of cholecalciferol in the treatment of muscular dystrophy, as an active agent or adjuvant in the regeneration of muscle tissue.

For the purposes of the present invention, the term "treatment" means the administration of cholecalciferol to a subject suffering from muscular dystrophy for the purpose of improving the overall condition of their muscle tissue, as well as for the purpose of slowing, relieving, reducing, and/or preventing any alteration of the functioning of their muscle tissue.

The term "regeneration" refers to any process of regenerative, reparative and protective stimulation of muscle tissue.

In another aspect, the present invention relates to a pharmaceutical composition or a food supplement for use in the treatment of muscular dystrophy, said composition or supplement comprising cholecalciferol as an active agent or adjuvant in the regeneration of muscle tissue and at least one suitable excipient.

BRIEF DESCRIPTION OF FIGURES

The characteristics and advantages of the present invention will become evident from the following detailed description, from the embodiments provided by way of illustrative and non-limiting examples, and from the attached Figures relating to the tests described in Example 1, where.

The red label with anti-Pax7 antibody is not very present and this is an indication of degeneration of the muscle fibres and absence of satellite cells. In blue, marked with DAPI, the nuclei are visible chaotically arranged also in the centre of the fibres, an indication of degeneration of the muscle tissue.

Figure 3:
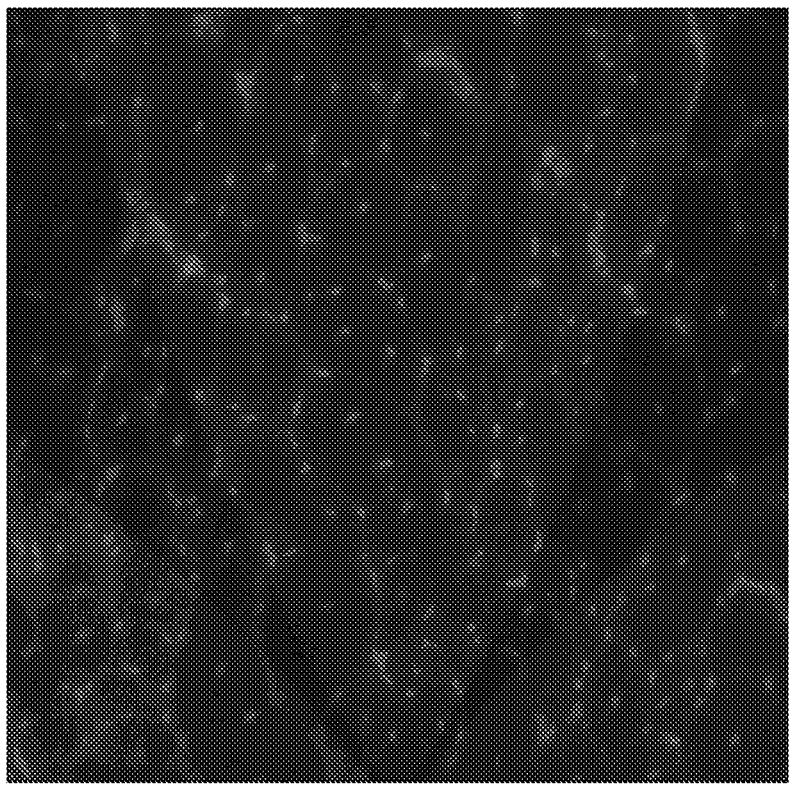

FIG. 3: Immunohistochemistry on sections from mdx mice treated with cholecalciferol at 24 weeks of treatment. The red labelling with anti-Pax7 antibody is clearly present and localized on the contours of the muscle fibres, where the satellite cells reside. In blue, marked with DAPI, the nuclei arranged both peripherally and in the centre of the fibres are visible.

Figure 4:
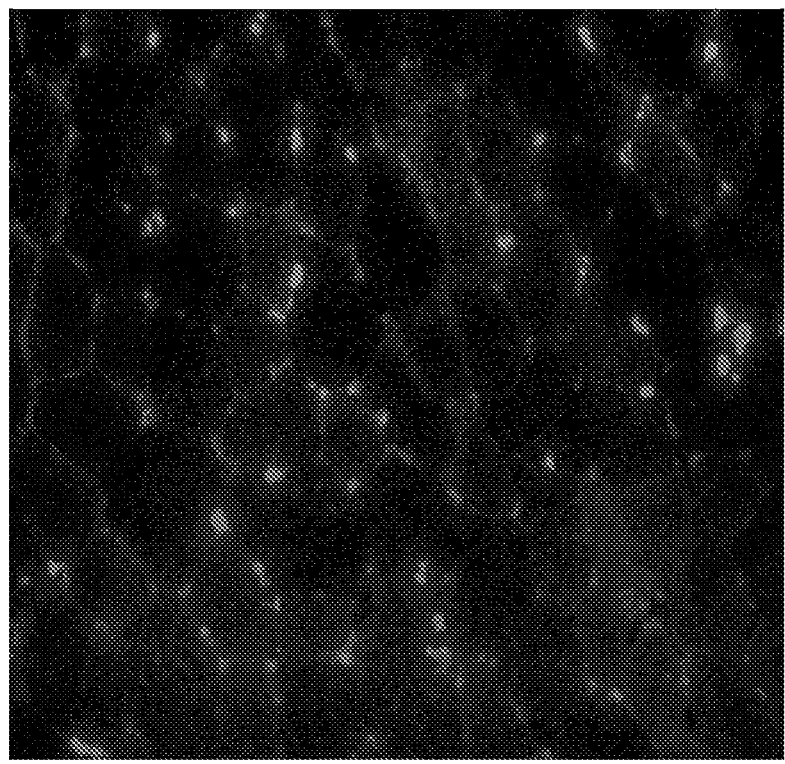

FIG. 4: Immunohistochemistry on sections from wild-type (WT) mice treated with the vehicle at 24 weeks of treatment. The labelling with anti-MyoD antibody, marker of muscle cell proliferation, in red, appears extensive.

Figure 5:
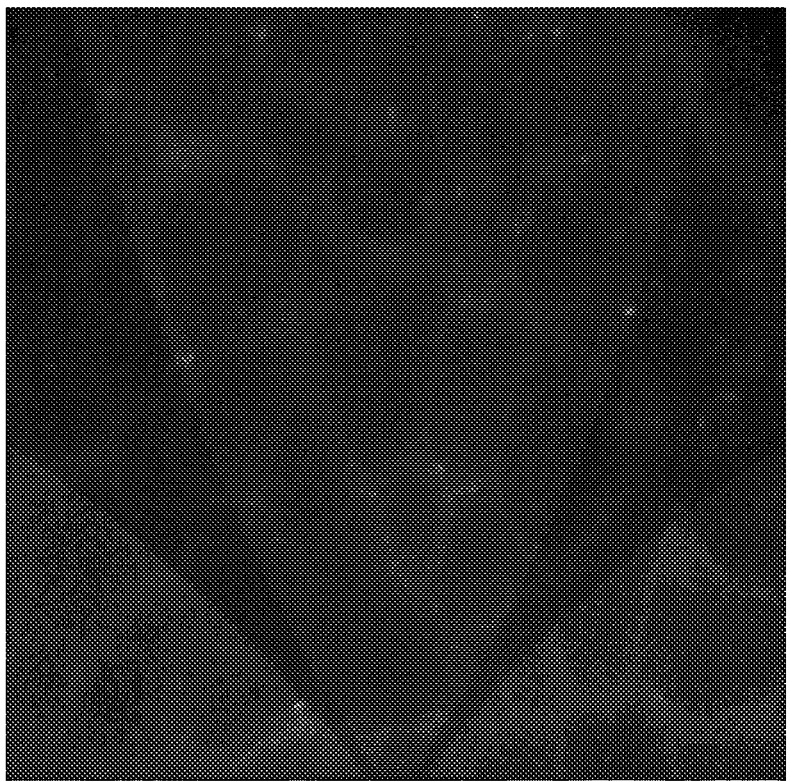

FIG. 5: Immunohistochemistry on sections from vehicle-treated mdx mice at 24 weeks of treatment. The labelling with anti-MyoD antibody, marker of muscle cell proliferation, in red, is almost absent.

Figure 6:
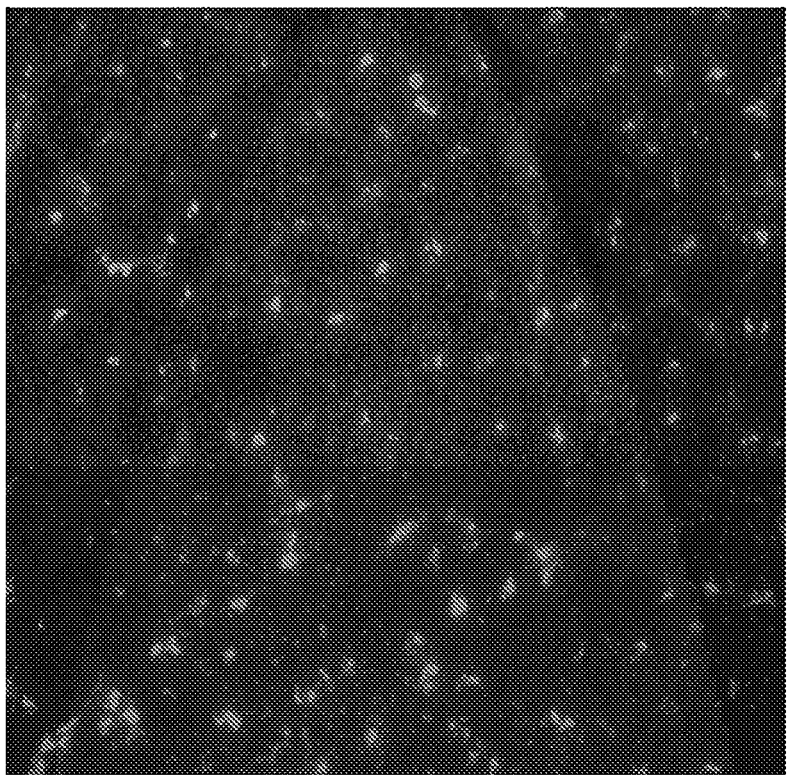

FIG. 6: Immunohistochemistry on sections from mdx mice treated with cholecalciferol at 24 weeks of treatment. The labelling with anti-MyoD antibody, marker of muscle cell proliferation, in red, appears extensive.

FIG. 7: Fluorescence microscopy. Cross section of muscle fibres from mice of the mdx group not treated at time 0. The nuclei are visible in blue (marked with DAPI), arranged centrally within the fibres (marked in red with anti-WGA antibody).

FIG. 8: Fluorescence microscopy. Cross-section of muscle fibres from mice of the wild-type group (WT) not treated at time 0. The nuclei are visible in blue (labelled with DAPI), arranged peripherally inside the fibres (labelled in red with anti-WGA antibody).

Figure 9:
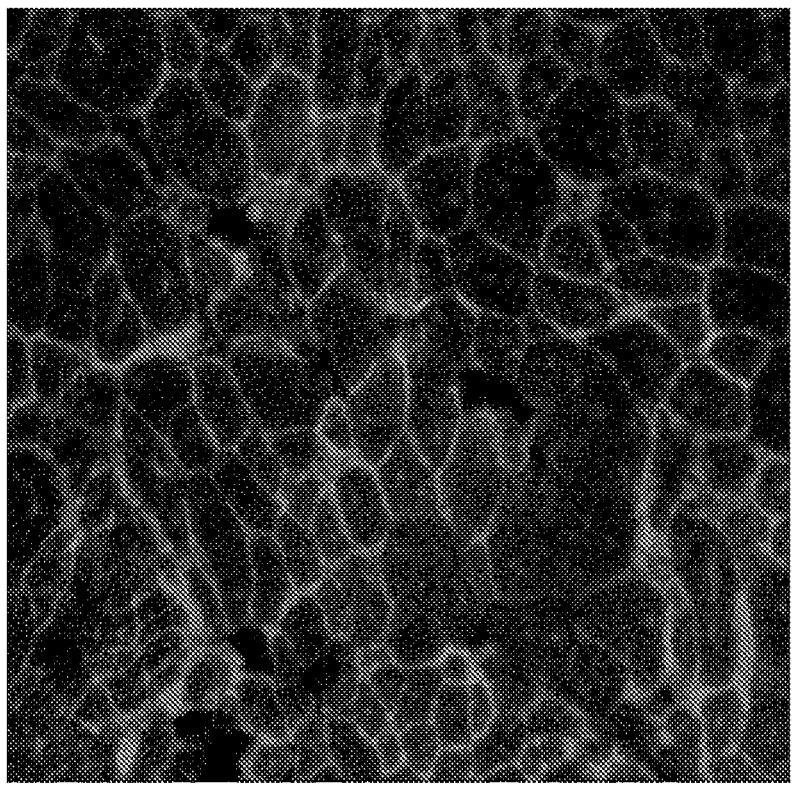

FIG. 9: Fluorescence microscopy. Cross-section of muscle fibres from mdx group mice treated with the vehicle at 12 weeks of treatment. The nuclei are visible in blue (marked with DAPI), arranged centrally within the fibres (marked in red with anti-WGA antibody). The fibres appear disrupted.

Figure 10:
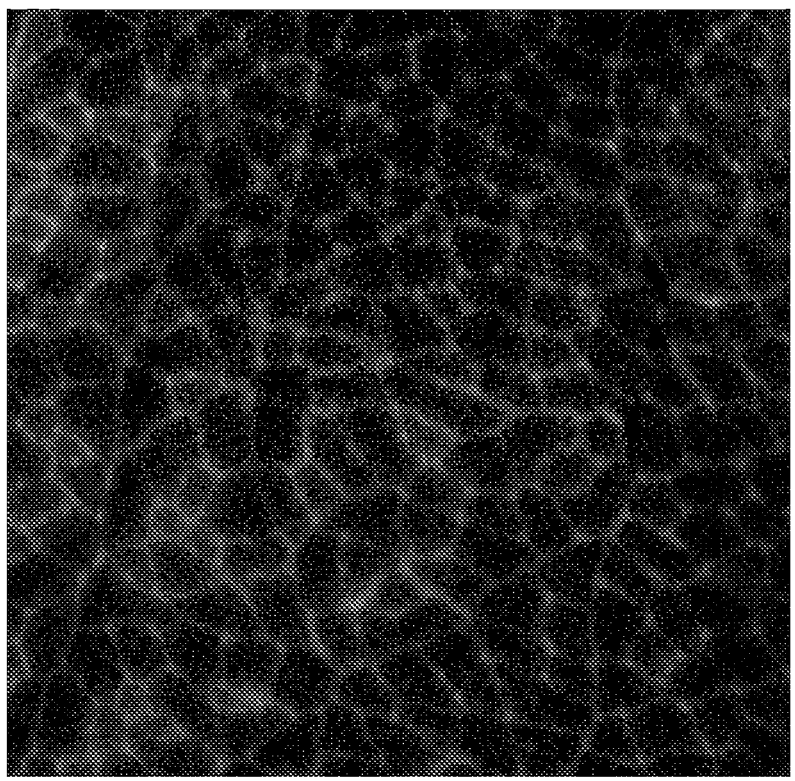

FIG. 10: Fluorescence microscopy. Cross-section of muscle fibres from wild-type (WT) mice treated with the vehicle at 12 weeks of treatment. The nuclei are visible in blue (marked with DAPI), arranged peripherally within the fibres (marked in red with anti-WGA antibody).

Figure 11:
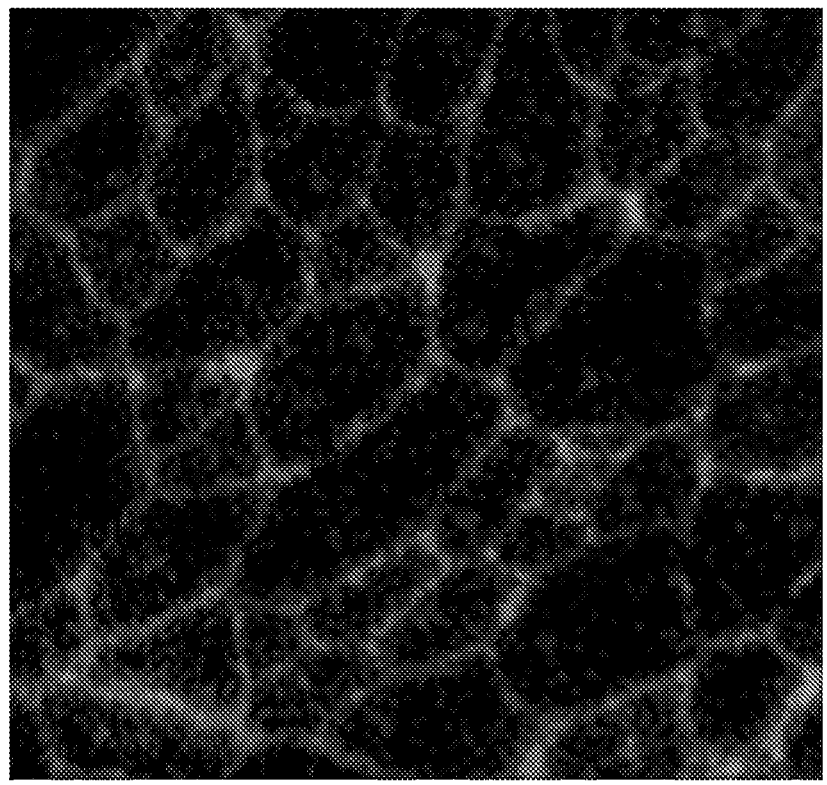

FIG. 11: Fluorescence microscopy. Cross-section of muscle fibres from mdx group mice treated with cholecalciferol at 12 weeks of treatment. The nuclei are visible in blue (marked with DAPI), arranged both centrally and peripherally within the fibres (marked in red with anti-WGA antibody). The fibres appear visibly less disrupted than in untreated control mdx mice.

DETAILED DESCRIPTION OF THE INVENTION

The present invention then relates to the use of cholecalciferol as an active agent or adjuvant in the regeneration of muscle tissue in subjects suffering from muscular dystrophies.

Cholecalciferol, or vitamin D3, is the natural compound of vitamin D, of animal/human origin. It is a pro-hormone, precursor of the two hydroxylated forms of vitamin D [25OHD and 1.25(OH)$_2$ D] and therefore it has to undergo two natural hydroxylation processes to be transformed in its metabolically active form.

For the purposes of the present invention, the term "cholecalciferol" includes all optical isomers, geometric isomers and stereoisomers, as well as their mixtures, such as mixtures of enantiomers, racemic mixtures and mixtures of diastereomers, as well as all their polymorphic forms, both amorphous and crystalline, and co-crystalline, as well as the anhydrous, hydrated and solvated forms, pharmaceutically acceptable salts, and mixtures thereof. As it will also be clear from the examples reported below, cholecalciferol has been shown to be an agent that can be advantageously used as an active or adjuvant in the regeneration of muscle tissue in subjects affected by muscular dystrophies. Therefore, the present invention is directed to cholecalciferol for use as an active agent or adjuvant in the treatment of muscular dystrophies, by regeneration of muscle tissue.

In particular, cholecalciferol has shown a marked activity in promoting the regeneration of muscle tissue in subjects suffering from muscular dystrophies. Cholecalciferol can therefore be effectively used as an active agent or adjuvant in muscle regeneration in subjects suffering from muscular dystrophies. The present invention therefore also concerns the use of a therapeutically effective amount of cholecalciferol as an active agent or adjuvant in muscle regeneration in subjects suffering from muscular dystrophies.

The Examples provided below have in fact shown how the muscle tissue of mdx mice treated with cholecalciferol is highly positive for anti-Pax6 and anti-MyoD antibodies, which are, respectively, the marker constitutively expressed by satellite cells (stem cells located in the lamina propria of muscle tissue) and the marker expressed by proliferating myoblasts. The absence or decrease of Pax 6 are indices of tissue degeneration and the absence of the MyoD marker is an indication of lack of tissue regeneration. The results of the immunohistochemical analysis show that the expression profiles of the Pax6 and MyoD markers of the mdx mice treated with cholecalciferol are completely comparable to those of healthy wild-type (WT) mice.

Moreover, cholecalciferol has also shown a marked activity in protection and regeneration of muscle tissue, therefore cholecalciferol can be effectively used also as active agent in the protection and regeneration of muscle tissue is subjects affected by muscular dystrophies. The present invention therefore also concerns the use of a therapeutically effective amount of cholecalciferol as an active agent or adjuvant in the protection and regeneration of muscle tissue in subjects suffering from muscular dystrophies.

In some embodiments, the present invention relates to the use of cholecalciferol as an active agent or adjuvant in the regeneration of muscle tissue, wherein said treatment comprises the administration of an amount that is therapeutically effective for muscle regeneration in subjects suffering from muscular dystrophy.

In other embodiments, the present invention relates to the use of cholecalciferol as an active agent or adjuvant in the protection of muscle tissue, wherein said treatment comprises the administration of a therapeutically effective amount for the protection of muscle tissue in subjects suffering from muscular dystrophies.

Preferably, cholecalciferol is to be administered in a dose ranging from 0.83 μg/kg to 21 μg/kg, more preferably from 4.2 μg/kg to 21 μg/kg, even more preferably 14.2 μg/kg. In other words, preferably cholecalciferol is to be administered in a dose from 33.3 IU/kg to 833.3 IU/kg of cholecalciferol, preferably from 166.6 IU/kg to 833.3 IU/kg, most preferably 560 IU/kg.

With "kg", it is meant kg of body weight of the subject affected by muscular dystrophy, according to the present invention, said subject being a human.

Advantageously, cholecalciferol can be administered only once a week, that is, in a single weekly administration, at the doses indicated above. This means that said cholecalciferol doses correspond to the weekly dose. Alternatively, cholecalciferol can be administered once a day, i.e. said weekly dose of cholecalciferol is to be administered in seven daily administrations, in a daily dose corresponding to one seventh of the weekly dose. In other embodiments, cholecalciferol can be administered only once a month, that is in a single monthly administration, in monthly doses corresponding to 4-5 times the weekly dose indicated above. In other words, cholecalciferol can be administered in a single monthly administration, in a monthly dose corresponding to 4-5 times the weekly dose. Preferably, said monthly dose is of 56.8 μg/kg or 2240 UI/kg.

Preferably, cholecalciferol is to be administered orally, by injection or subcutaneously, more preferably orally. With the exception of particular clinical conditions (e.g. malabsorption syndromes), the oral route of administration is preferable, as it is superior in terms of efficacy in increasing serum 25OHD compared to the intramuscular formulation. In another aspect, the present invention relates to a pharmaceutical composition or a food supplement, comprising cholecalciferol and at least one suitable excipient, for use in the regeneration of muscle tissue in subjects suffering from muscular dystrophies. In yet another aspect, the present invention relates to a pharmaceutical composition or a food supplement, comprising cholecalciferol and at least one suitable excipient, for use in the protection of muscle tissue in subjects suffering from muscular dystrophies.

In a further aspect, the present invention relates to a pharmaceutical composition or a food supplement, comprising cholecalciferol and at least one suitable excipient, for use in the regeneration and protection of muscle tissue in subjects suffering from muscular dystrophies.

In some embodiments, the present invention relates to a pharmaceutical composition or a food supplement, comprising cholecalciferol and at least one suitable excipient, for use in muscle regeneration, wherein said use comprises the administration of a pharmaceutical composition or food supplement comprising an amount of cholecalciferol that is therapeutically effective for the regeneration of muscle tissue in subjects suffering from muscular dystrophies.

In other embodiments, the present invention relates to a pharmaceutical composition or a food supplement, comprising cholecalciferol and at least one suitable excipient, for use in the protection of muscle tissue, wherein said use comprises the administration of a pharmaceutical composition or food supplement comprising a quantity of therapeutically effective cholecalciferol for the protection of muscle tissue in subjects suffering from muscular dystrophies.

The pharmaceutical composition, as well as the food supplement of the invention, can be administered orally, by injection or subcutaneously.

In a preferred embodiment, said pharmaceutical composition or dietary supplement is to be administered orally.

When the pharmaceutical composition or food supplement is to be administered orally, it is preferably in the form of an orodispersible solid preparation, gel, capsule, tablet, powder, granulate, solution, suspension, emulsion or tincture.

The pharmaceutical composition or food supplement of the invention to be administered orally in the form of an orodispersible solid preparation, gel, capsule, tablet, powder, granulate, solution, suspension, emulsion or tincture, is preferably administered in a dose such as to provide from 0.83 µg/kg to 21 µg/kg, more preferably from 4.2 µg/kg to 21 µg/kg, most preferably 14.2 µg/kg. That is, said pharmaceutical composition or food supplement of the invention to be administered orally in the form of an orodispersible solid preparation, gel, capsule, tablet, powder, granulate, solution, suspension, emulsion or tincture, is preferably administered in a dose such as to provide from 33.3 IU/kg to 833.3 IU/kg of cholecalciferol, preferably from 166.6 IU/kg to 833.3 IU/kg, even more preferably 560 IU/kg.

Advantageously, the pharmaceutical composition or the food supplement of the invention can be administered only once a week, at the doses indicated above, or once a month, in a dose corresponding to 4-5 times the doses indicated above, preferably in a dose of 56.8 µg/kg or 2240 IU/kg. In preferred embodiments, the pharmaceutical composition or the food supplement of the invention to be administered orally, in the form of a solution, suspension, emulsion, gel o tincture, comprises cholecalciferol at a concentration from 14,000 UI/mL to 20,000 UI/mL.

Said pharmaceutical composition or food supplement of the invention can advantageously be in unit dose form.

Said pharmaceutical composition or food supplement of the invention, also in unit dose form, further include at least one suitable excipient. The term "excipient" means a compound or a mixture of compounds suitable for pharmaceutical or food use, respectively. For example, an excipient for use in a pharmaceutical or food formulation generally must not cause an adverse response in a subject, nor must it significantly inhibit the efficacy of the cholecalciferol contained therein. Suitable excipients are acidifiers, acidity regulators, anti-caking agents, antioxidants, bulking agents, resistance agents, gelling agents, glazing agents, modified starches, sequestrants, thickeners, sweeteners, thinners, disaggregants, glidants, dyes, binders, lubricants, stabilizers, adsorbents, humectants, flavours, film-forming substances, emulsifiers, wetting agents, release retardants and mixtures thereof. Preferably, said excipients are olive oil, mineral oil, liquid paraffin, white petrolatum, polyoxyethylene, emulsifying wax, stearyl alcohol, isostearyl alcohol, cetylstearyl alcohol, stearic acid, glyceryl stearate, sodium lauryl sarcosinate, glycerine, diethylene glycolmonoethyl ether, polyethylene glycol, polyethylene glycol, polyethylene glycol stearates, Carbopol, carbomers, Poloxamer 407, Macrogol 400, purified bentonite, myristyl propionate, dimethicone, titanium dioxide, anionic, cationic and non-ionic surfactants, water, potassium sorbate, sodium benzoate, ε-polylysine, sucralose, maltodextrin, citric acid, sodium carbonate, calcium carbonate, magnesium carbonate, magnesium stearate, natural starch, partially hydrolysed starch, modified starch, lactose, calcium phosphate, calcium carbonate, calcium sulfate, polyvinylpyrrolidone, silica, colloidal silica, precipitated silica, magnesium silicates, aluminium silicates, sodium lauryl sulfate, magnesium lauryl sulfate, methacrylate copolymers, sodium dehydroacetate, xanthan gum, guar gum, tara gum, carob gum, fenugreek gum, Arabic gum, alginic acid, sodium alginate, propylene glycol alginate, sodium croscarmellose, polyvinylpolypyrrolidone, glyceryl behenate, indigo carmine, cellulose, modified cellulose, calcium carboxymethylcellulose, sodium carboxymethylcellulose, microcrystalline cellulose, ethyl cellulose, gelatine, hydroxyethyl cellulose, hydroxypropyl cellulose, polydextrose, carrageenan, methylcellulose, sucrose, sucrose esters, sorbitol, xylitol, dextrose, maltitol, tragacanth gum, pectin, agar-agar, carboxypolymethylene, hydroxypropyl methylcellulose, tragacanth gum, mannitol, or mixtures thereof. In some embodiments, the pharmaceutical composition or the food supplement of the invention essentially consists of cholecalciferol and at least one suitable excipient. The expression "essentially consists of" means that cholecalciferol is the only active ingredient in muscle regeneration to be present in the composition or supplement, while optional additional components or excipients do not interfere with its action. It should be understood that all the aspects identified above as preferred and advantageous for the use of cholecalciferol, the composition or the supplement, are to be considered similarly preferred and advantageous also for these embodiments.

In other embodiments, the pharmaceutical composition or food supplement of the invention consists of cholecalciferol and at least one suitable excipient.

All the pharmaceutical compositions or food supplements described above can be prepared by methods known in the art.

It should be understood that all the possible combinations of the preferred aspects of cholecalciferol, of the products containing it and of the respective uses, as indicated above, are also hereby described, and therefore similarly preferred.

It should also be understood that all the aspects identified as preferred and advantageous for cholecalciferol and its products, are to be considered similarly preferred and advantageous also for their preparation and uses. The effectiveness of cholecalciferol as an active agent or adjuvant in muscle regeneration in subjects suffering from muscular dystrophies will also be clear from the examples given below.

Furthermore, cholecalciferol is normally stored in adipose tissue, where it creates storages from which it is slowly released. Precisely for this reason, it has a rather short blood half-life ($T_{1/2}$ estimated at 19-25 hours), while its functional half-life (several weeks) is much longer (related to slow release). The high functional half-life (slow release by adipose tissue) makes cholecalciferol an extremely flexible and adaptable active agent in clinical practice, allowing even intermittent administration regimens.

Below are working examples of the present invention provided for illustrative and non-limiting purposes.

EXAMPLES

Example 1— Evaluation of Efficacy of Oral Administration of Cholecalciferol in an in Vivo Mouse Mode of Muscular Dystrophy (Mdx Mice)

For the study, it was chosen as experimental model the mdx (Muscular Dystrophy X-linked) mouse, which has long been used to evaluate the efficacy of drugs against muscular dystrophy and other degenerative diseases that affect skeletal muscles, inducing functional loss. These mice represent the reference animal model for clinical projections, also because they made it possible to overcome the obstacle of the limited availability of human biopsy material for experimental purposes.

The model responds to both steroidal and non-steroidal anti-inflammatory and immunosuppressive treatments and it is also used to study the differential gene and protein expression induced by the various treatments. The test system altogether consisted in 50 C57BL/10ScSn-Dmdxdx/J male mice and 27 C57/BL male mice of about 4-5 weeks of age.

After a short pre-housing period (about 4 days after arrival in the animal enclosure), the animals were subjected to baseline behavioural analyses, as described hereafter. The start time of the analyses, after the pre-housing period, is defined zero time (t=0).

Mice were also subjected to physical exercise with a rotating treadmill (Ugo Basile, Milan) for 15 minutes twice a week at a speed of 12 m/min, to standardize the pathology.

The animals were treated orally according to the scheme shown in table 1.

TABLE 1

| Group N° | N° subjects per group | Genotype | Type of treatment | Dosage and administration route | Posology and duration of treatment |
|---|---|---|---|---|---|
| 1 | 10 | C57BL/10Sc Sn-Dmdxdx/J | N/A Early disease Time 0 | N/A | N/A Sacrificed after pre-housing period (t = 0) |
| 2 | 9 | C57 BL wild type | N/A Wild-type (WT) Time 0 | N/A | N/A Sacrificed after pre-housing period (t = 0) |
| 3 | 9 | C57 BL wild-type (WT) | Vehicle (olive oil) | 50 µl of volume per os | Once per week for 12 weeks |
| 4 | 10 | C57BL/10Sc Sn-Dmdxdx/J | Vehicle (olive oil) | 50 µl of volume per os | Once per week for 12 weeks |
| 5 | 10 | C57BL/10Sc Sn-Dmdxdx/J | Cholecalciferol | 175 µg/kg/day (7000 IU/day) in 50 µl of volume per os | Once per week for 12 weeks |
| 6 | 9 | C57 BL wild-type (WT) | Vehicle (olive oil) | 50 µl of volume per os | Once per week for 24 weeks |
| 7 | 10 | C57BL/10Sc Sn-Dmdxdx/J | Vehicle (olive oil) | 50 µl of volume per os | Once per week for 24 weeks |
| 8 | 10 | C57BL/10Sc Sn-Dmdxdx/J | Cholecalciferol | 175 µg/kg/day (7000 IU/day) in 50 µl of volume per os | Once per week for 24 weeks |

Animals of groups 1 and 2 have been sacrificed immediately after the pre-housing period (t=0) for the established analyses.

At the end of treatment (t=12 or t=24) animals have been sacrificed by bleeding under deep isoflurane anaesthesia.

Four Limb Hang Test

This test was performed at the beginning and at the end of the trial (baseline and final). It is performed using a device that uses a steel grid to measure the mouse's ability to support itself on all four limbs, opposing the force of gravity. The animal is placed on the grid (40×40 cm, delimited by iron strips placed perpendicular to the grid and 5 cm high, with 1 cm squares formed by 1 mm diameter steel wire) which is inverted so that the animal finds itself upside down and hangs on with its paws, about 30 cm from the floor. A layer of soft litter is placed on the floor so that the animal does not feel pain at the time of a possible fall. The grid is kept in position for a maximum of 5 minutes and the time, in seconds, during which the animal is able to hang with its paws is recorded.

Results

The results of test are shown in the following table 2 and are expressed in seconds and normalized for the animal's weight. Groups 1-8 reported herein are those described in table 1.

TABLE 2

| N° Gruppo | Time in seconds (normalized for the animal's weight) t = 0 | Time in seconds (normalized for the animal's weight) t = 12 weeks | Time in seconds (normalized for the animal's weight) t = 24 weeks |
|---|---|---|---|
| 1 | 0.53 | — | — |
| 2 | 9.8 | — | — |
| 3 | 3.2 | 3 | — |
| 4 | 0.8 | 0.6 | — |
| 5 | 0.9 | 0.8 | — |
| 6 | 7.5 | 5.3 | 1.9 |
| 7 | 1.5 | 0.8 | 0.5 |
| 8 | 1.7 | 1.2 | 0.9 |

Wild-type (WT) animals showed the longest resistance, while mdx animals untreated or treated with the sole vehicle generally resisted for shorter times in the test.

The treatment with cholecalciferol allowed mdx animals to remain clinging to the grid for longer times than the untreated ones, at all analysis intervals, with very significant increases in resistance to detachment from the grid, in terms of time, even by 80% in the case of test at 24 weeks.

Histopathologic Analyses

These analyses were performed on the material taken during necropsy performed after the sacrifice of the animals of groups 7 and 8. In particular, the quadriceps femoris, the diaphragm and the anterior tibial muscle were collected.

The samples taken and fixed were decalcified, embedded in paraffin according to the known technique, cut into 5-7 μm thick sections and stained with haematoxylin-eosin. The following forms of alteration were evaluated at the muscle tissue level, each of which was classified according to a grade from 0 (absent) to 3 (very high):

Atrophy
Degeneration
Inflammation
Oedema
Presence of adipose tissue
Hypertrophy
Regeneration
Mineralization Results Test results are shown in table 3 that follows.

TABLE 3

| Alteration form | Medium Grading Group N° 7 C57BL/10ScSn-Dmdxdx/J Treated with vehicle t = 24 weeks | Medium Grading Group N° 8 C57BL/10ScSn-Dmdxdx/J Treated with cholecalciferol 175 μg/kg/day once a week t = 24 weeks |
|---|---|---|
| Atrophy | 2.1 | 0.44 |
| Degeneration | 2.6 | 0 |
| Inflammation | 1.2 | 0 |
| Oedema | 1.3 | 0.44 |
| Presence of adipose tissue | 1.6 | 0.11 |
| Hypertrophy | 1.6 | 2.11 |
| Regeneration | 1.4 | 2.66 |
| Mineralization | 0.7 | 0.33 |

Microscopic examination of muscle tissue stained with haematoxylin-eosin showed signs of significantly high muscle fibre atrophy, with areas of necrosis and fibrosis in all mdx mice treated with the vehicle alone. In these groups the areas of degeneration and those in which adipose tissue replaces muscle were very extensive. Many samples also had oedematous areas with extensive inflammation. In particular, the diaphragm muscle of mdx animals showed a high degree of fibrosis and its thickness was considerably more marked. Mdx mice treated with cholecalciferol for 24 weeks showed instead areas of regeneration and hypertrophy, and only in few cases muscular atrophy, moreover at low levels.

In Table 3 it is evident the increase in the values of the regeneration and hypertrophy parameters in group 8, treated with cholecalciferol compared to group 7 treated with the vehicle alone and, in parallel, the decrease in the values of the parameters related to degenerative, inflammatory and atrophic phenomena.

Immunohistochemistry

Skeletal muscle growth and regeneration are attributable to satellite cells, which are stem cells resident in the basal lamina surrounding each myofiber. The expression of Pax7 (Paired-Box Transcription Factor 7) is constitutive, that is, this factor is expressed in these cells both in the quiescent and in the activation phase. When satellite cells are activated, they also co-express MyoD, which correlates with active muscle regeneration.

The expression of Pax7 was then analysed for the identification of satellite cells (progenitors) located under the basal lamina of myofibers, and of MyoD, expressed by myoblasts during proliferation.

Analyses were performed on the groups after 24 weeks of treatment.

Samples for immunohistochemistry were included in OCT, placed in isopentane, frozen with liquid nitrogen and kept at −80° C. Anti-Pax7 antibodies were used to label satellite cells and anti-MyoD for myoblasts.

Results

Figure 1:
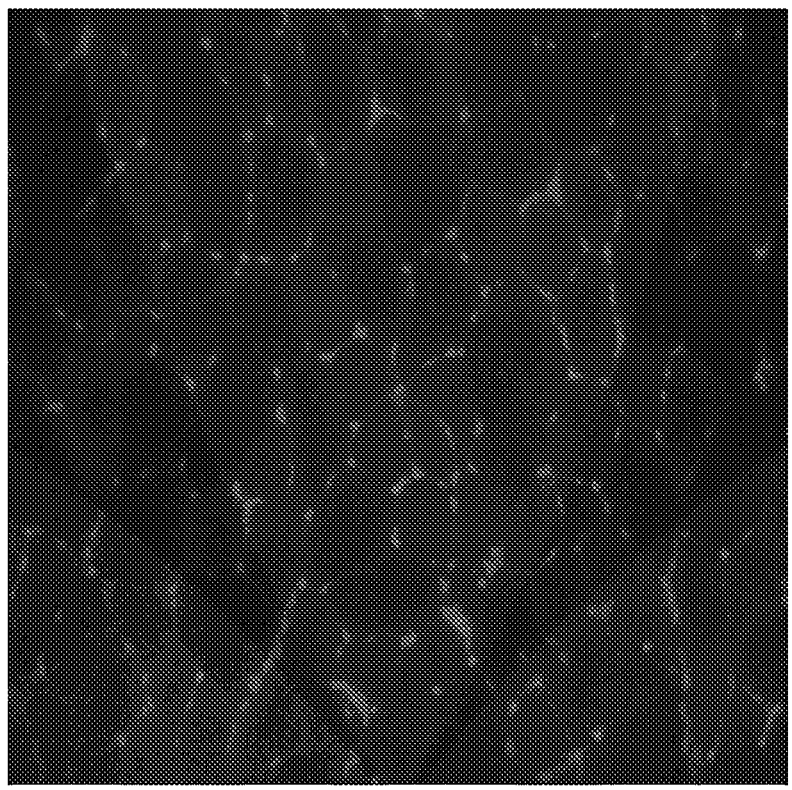
FIG. 1: Immunohistochemistry on sections from wild-type (WT) mice treated with vehicle (olive oil) at 24 weeks of treatment. The contours of the muscle fibres, where the satellite cells are located, are marked with anti-Pax7 antibody in red. In blue, labelled with DAPI, the cell nuclei of healthy muscle cells are visible, which are peripherally located.
Figure 2:
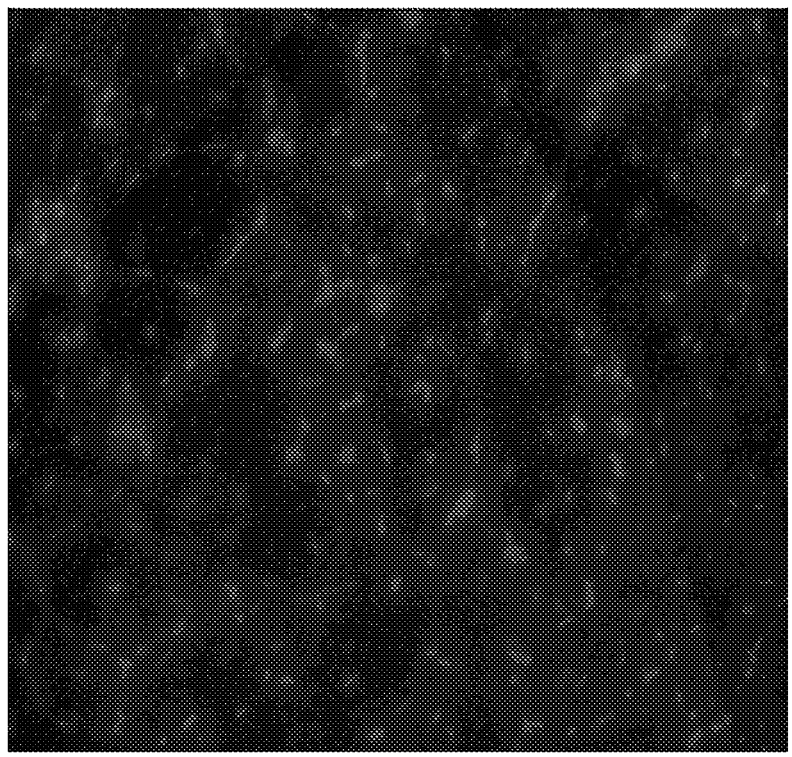
FIG. 2: Immunohistochemistry on sections from vehicle-treated mdx mice at 24 weeks of treatment.

In wild-type (WT) animals, treated with vehicle, Pax7 visibly marked the surrounds of muscular fibres, highlighting the presence of satellite cells (FIG. 1). In contrast, the labelling significantly decreased in mdx mice treated with the vehicle in the absence of cholecalciferol (FIG. 2), while it appeared more evident in mdx animals treated with cholecalciferol (FIG. 3).

The presence of MyoD was very evident in wild-type mice (FIG. 4), while it was almost absent in mdx mice (FIG. 5). Treatment with cholecalciferol, on the other hand, restored the expression of MyoD to levels similar to those of wild-type mice (FIG. 6), thus indicating a significant activity of cholecalciferol in muscle regeneration.

Fluorescence Microscopy

In fluorescence microscopy analyses DAPI staining (blue) was used for nuclei, while an anti-WGA antibody (WGA, or wheat germ agglutinin, Alexa Fluor® 594 conjugate), which stains cell membranes in red, was used to mark muscle fibres.

Results

The fluorescence analysis showed that the muscle tissue of mdx mice sacrificed at time 0 (FIG. 7) is not well differentiated since the nuclei of the myocytes that make up the fibres are located in a central and not peripheral position, which happens instead in the case of well differentiated tissue. On the contrary, the group of wild-type animals (WT) at time 0 showed a well differentiated tissue, with the cell nuclei located peripherally within the fibres (FIG. 8). The same analogous considerations apply to the mdx group (FIG. 9) and to the wild-type (WT) group at 12 weeks of treatment with the vehicle alone (FIG. 10). Furthermore, the mdx mice treated with the vehicle for 12 weeks also showed an altered and rather disrupted structure of the muscle fibres. On the other hand, the mdx mice treated with cholecalciferol at 12 weeks of treatment showed cell nuclei distributed both centrally and peripherally and less disrupted muscle fibres (FIG. 11), i.e. a muscle tissue with a certainly more intact structure than that which characterized the group of untreated mdx mice.

Example 2— Pharmaceutical Composition Comprising Cholecalciferol for Oral Use in the Form of a Solution In order to make pharmaceutical compositions in the form of a solution for oral use, cholecalciferol was mixed with suitable excipients.

The compositions made contained a unit dosage of about 50,000 IU and 35,000 IU per bottle.

The quantities of excipients contained in each bottle are indicated in the following tables 4a and 4b, respectively.

TABLE 4a

| Component | Unitary amount |
| --- | --- |
| Cholecalciferol | 50,000 UI |
| Refined olive oil | at volume up to 2.5 mL |

TABLE 4b

| Component | Unitary amount |
| --- | --- |
| Cholecalciferol | 35,000 UI |
| Refined olive oil | at volume up to 2.5 mL |

After having introduced refined olive oil into a dissolution tank heated to 40° C.±3° C. (checking that the temperature never exceeded 45° C.), cholecalciferol was added under nitrogen, stirring until complete dissolution (at least 60 minutes). The mixture was then cooled to about 27° C. (±3° C.) and filtered under nitrogen at the maximum pressure of 0.8 atm in the tank.

The filtered solution was finally automatically dosed inside amber III type bottles and sealed inside.

Example 3—Pharmaceutical Compositions Comprising Cholecalciferol for Oral Use in the Form of a Rigid Gel Capsule In order to make a pharmaceutical composition in the form of a hard capsule for oral use, cholecalciferol was mixed with suitable excipients.

The compositions made contained a unit dosage of about 50,000 IU and 35,000 IU per capsule.

The quantities of excipients contained in each capsule are indicated in the following tables 5a and 5b, respectively.

TABLE 5a

| Component | Unitary amount (mg) |
| --- | --- |
| Cholecalciferol | 1.250 mg (equivalent to 50,000 UI) |
| Refined olive oil | 181.150 mg |

TABLE 5b

| Component | Unitary amount (mg) |
| --- | --- |
| Cholecalciferol | 0.875 mg (equivalent to 35.000 UI) |
| Refined olive oil | 181.525 mg |

Cholecalciferol was added to the refined olive oil in a dissolution tank, under nitrogen, maintaining it stirred until complete dissolution (for at least 60 minutes).

Capsules were filled, still under nitrogen, by means of automatic machines, with 2004, of the cholecalciferol solution so prepared.

The capsules were then sealed with banding by means of a gelatine band and packaged in PVC/PVDC/Al blisters by means of an automatic blistering machine.

CONCLUSIONS

The studies performed have shown an effect of cholecalciferol on the musculature of mice with dystrophy, both in terms of functional performance and relative to the morphology of the tissue itself.

The invention claimed is:

1. A method of treating muscular dystrophy, the method comprising the step of
administering to patients in need thereof a therapeutically effective amount of cholecalciferol as an active agent or adjuvant in the regeneration of muscle tissue, wherein said therapeutically effective amount of cholecalciferol is a dose of 14.2 µg/kg, or 560 IU/kg.

2. The method of claim 1, wherein said muscular dystrophy is Duchenne muscular dystrophy (DMD), Becker's muscular dystrophy or Emery-Dreyfuss muscular dystrophy.

3. The method of claim 1, wherein said cholecalciferol dose corresponds to the weekly dose.

4. The method of claim 3, wherein said dose of cholecalciferol is to be administered in a single weekly administration, or is to be administered in seven daily administrations with a daily dose corresponding to one seventh of the weekly dose.

5. The method of claim 3, wherein said weekly dose of cholecalciferol is to be administered in a single monthly administration with a dose corresponding to 4-5 times the weekly dose.

6. The method of claim 1, wherein the cholecalciferol is to be administered orally, by injection or subcutaneously.

7. The method of claim 1, wherein the therapeutically effective amount of cholecalciferol is to be administered in the form of pharmaceutical composition or food supplement comprising cholecalciferol and at least one suitable excipient.

8. The method of claim 7, wherein said pharmaceutical composition or food supplement is to be administered orally, and is in the form of an orodispersible solid preparation, gel, capsule, tablet, powder, granulate, solution, suspension, emulsion or tincture.

9. The method of claim 8, in the form of a solution, suspension, gel emulsion or tincture, comprising cholecalciferol in a concentration of 14,000 IU/mL to 20,000 IU/mL.

* * * * *